(12) United States Patent
Suzuki et al.

(10) Patent No.: US 9,463,088 B2
(45) Date of Patent: Oct. 11, 2016

(54) INTRAOCULAR LENS DESIGN METHOD AND INTRAOCULAR LENS

(75) Inventors: Takayoshi Suzuki, Shizuoka (JP); Haruo Ishikawa, Tokyo (JP)

(73) Assignee: KOWA COMPANY, LTD., Aichi (JP)

( * ) Notice: Subject to any disclaimer, the term of this patent is extended or adjusted under 35 U.S.C. 154(b) by 0 days.

(21) Appl. No.: 14/009,656

(22) PCT Filed: Apr. 2, 2012

(86) PCT No.: PCT/JP2012/059018
§ 371 (c)(1),
(2), (4) Date: Oct. 3, 2013

(87) PCT Pub. No.: WO2012/137748
PCT Pub. Date: Oct. 11, 2012

(65) Prior Publication Data
US 2014/0025165 A1    Jan. 23, 2014

(30) Foreign Application Priority Data
Apr. 5, 2011    (JP) .................................. 2011-083766

(51) Int. Cl.
G02C 7/02    (2006.01)
A61F 2/16    (2006.01)

(52) U.S. Cl.
CPC ............. *A61F 2/1637* (2013.01); *G02C 7/027* (2013.01); *A61F 2240/002* (2013.01)

(58) Field of Classification Search
None
See application file for complete search history.

(56) References Cited

U.S. PATENT DOCUMENTS

| | | |
|---|---|---|
| 2002/0071092 A1 | 6/2002 | Suzaki et al. |
| 2002/0105617 A1 | 8/2002 | Norrby et al. |
| 2002/0122153 A1 | 9/2002 | Piers et al. |
| 2003/0063254 A1 | 4/2003 | Piers et al. |
| 2004/0057011 A1 | 3/2004 | Suzaki et al. |
| 2004/0088050 A1 | 5/2004 | Norrby et al. |
| 2004/0156014 A1 | 8/2004 | Piers et al. |

(Continued)

FOREIGN PATENT DOCUMENTS

| | | |
|---|---|---|
| JP | 2003-534565 A | 11/2003 |
| JP | 2004-524072 A | 8/2004 |

(Continued)

OTHER PUBLICATIONS

Extended European Search Report dated Mar. 17, 2015 in corresponding European Patent Application No. 12767366.3.

(Continued)

*Primary Examiner* — David H. Willse
*Assistant Examiner* — Javier Blanco
(74) *Attorney, Agent, or Firm* — Knobbe Martens Olson & Bear LLP (57) ABSTRACT

Provided is a technique which, in the design of intraocular lenses, simplifies design work and makes it possible for aberration of the entire eyeball to more precisely match a target value when the designed intraocular lens is inserted into a patient's eye. This intraocular lens design method involves deriving an intraocular lens aberration target value from the aberration of the cornea and anterior chamber and a set value of the total eyeball aberration (S102), and determining an intraocular lens shape such that the at least the aberration of the intraocular lens coincides with the target value (S103-S107). The intraocular lens aberration is set to an intraocular lens aberration for which prescribed convergent light is incident to the intraocular lens (S104).

8 Claims, 6 Drawing Sheets

(56) References Cited

U.S. PATENT DOCUMENTS

| | | |
|---|---|---|
| 2004/0183996 A1 | 9/2004 | Piers et al. |
| 2006/0158611 A1 | 7/2006 | Piers et al. |
| 2006/0244905 A1 | 11/2006 | Piers et al. |
| 2006/0244906 A1 | 11/2006 | Piers et al. |
| 2007/0121064 A1 | 5/2007 | Norrby et al. |
| 2007/0188700 A1 | 8/2007 | Piers et al. |
| 2007/0258044 A1 | 11/2007 | Norrby et al. |
| 2008/0198326 A1 | 8/2008 | Piers et al. |
| 2009/0036980 A1 | 2/2009 | Norrby et al. |
| 2009/0125105 A1 | 5/2009 | Lesage et al. |
| 2009/0281552 A1 | 11/2009 | Hiramatsu et al. |
| 2011/0082542 A1 | 4/2011 | Norrby et al. |
| 2011/0157548 A1 | 6/2011 | Lesage et al. |
| 2012/0029630 A1 | 2/2012 | Piers et al. |
| 2012/0059463 A1 | 3/2012 | Norrby et al. |

FOREIGN PATENT DOCUMENTS

| | | |
|---|---|---|
| JP | 2004-528897 A | 9/2004 |
| JP | 2006-519031 A | 8/2006 |
| JP | 2009034451 | 2/2009 |
| JP | 4536907 B2 | 9/2010 |
| WO | 01/89424 | 11/2001 |
| WO | 02/051338 | 7/2002 |
| WO | 2006/088440 | 8/2006 |
| WO | WO 2007/128423 A1 | 11/2007 |
| WO | WO 2010/064278 A1 | 6/2010 |

OTHER PUBLICATIONS

Office Action dated Aug. 19, 2015 in corresponding Australian Patent Application No. 2012239659.

Office Action dated Sep. 25, 2015 in corresponding Chinese Patent Application No, 201280017156.X.

Notice of Reason for Rejection dated Jan. 19, 2016 in corresponding Japanese Patent Application No. 2013-508866.

Office Action dated Apr. 5, 2016 in corresponding Russian Patent Application No. 2013145313/14(070062).

Notice of Reason for Rejection dated Jul. 26, 2016 in corresponding Japanese Patent Application No. 2013-508866.

INTRAOCULAR LENS DESIGN METHOD AND INTRAOCULAR LENS

CROSS-REFERENCE TO RELATED APPLICATIONS

This application is the U.S. National Phase under 35 U.S.C. §371 of International Application PCT/JP2012/059018, filed Apr. 2, 2012, which was published in a non-English language, which claims priority to JP Application No. 2011-083766, filed Apr. 5, 2011.

TECHNICAL FIELD

The present invention relates to an intraocular lens design method for inserting an intraocular lens into an eyeball of a patient and an intraocular lens designed using the design method.

BACKGROUND ART

Conventionally, a treatment has been performed, in which an incision is formed in ocular tissue such as the cornea (sclera) and an anterior capsule portion of an eyeball, an intracapsular crystalline lens is extracted and removed through the incision, and then an intraocular lens that replaces a crystalline lens is inserted into the eye through the incision to be disposed in the anterior capsule.

The intraocular lens having a power consistent with a diopter scale of a patient is inserted into the eyeball of the patient by the surgery. If the diopter scale of the patient is not consistent with the power of the inserted intraocular lens, eyesight of the patient may not be recovered sufficiently even after the surgery, therefore, it is necessary to arrange the intraocular lenses having standards with different powers (focal distance) between +30D and +6D, for example, and to select the most appropriate one. In addition, with respect to the arranged intraocular lenses of all of the standards, the aberration of the whole eyeball after the insertion of the intraocular lens is required to be set to a desired value.

Here, the following relation is satisfied between the aberration of the whole eyeball, the aberration of the cornea and the anterior chamber portion, and the aberration of the crystalline lens and posterior chamber portion.

Aberration of crystalline lens and posterior chamber portion=Aberration of whole eyeball−Aberration of cornea and anterior chamber portion     (1)

Further, in an eyeball, when the crystalline lens is removed, and then the intraocular lens instead of the crystalline lens is inserted into the eyeball, similarly, the following relation is satisfied between the aberration of the whole eyeball, the aberration of the cornea and the anterior chamber portion, and the aberration of the intraocular lens.

Aberration of intraocular lens=Aberration of whole eyeball−Aberration of cornea and anterior chamber portion     (2)

Upon designing the intraocular lens, a target value of the aberration of the intraocular lens is determined on the basis of formula (2) and a shape of the intraocular lens is determined so as to be the determined aberration, (furthermore, the aberration in the above formula represents a wavefront aberration expressed by Zernike polynomials). In the related art, however, with respect to the aberration in each term of formula (2), a numerical value of a case where parallel light enters each element has been used. Meanwhile, in an actual usage environment, convergent light due to the cornea and the anterior chamber portion enters the intraocular lens. Accordingly, when the aberration in the whole eyeball of a patient is measured after the intraocular lens designed by the method of the related art is inserted into the eyeball, there has been a case where the value of the aberration deviates from a set value.

CITATION LIST

Patent Literature

Patent Literature 1: JP 4536907 B1
Patent Literature 2: JP 2004-524072 W
Patent Literature 3: JP 2004-528897 W

SUMMARY OF INVENTION

Technical Problem

The present invention has been made in view of the above problems in the related art. An object of the present invention is to provide a technique capable of simplifying a design work in a design of an intraocular lens and capable of conforming the aberration in the whole eyeball to a target value with higher accuracy at the time of inserting the designed intraocular lens into an eyeball of a patient.

Solution to Problem

The preferred advantage of the present invention is to use a value of a case where predetermined convergent light enters as an aberration of an intraocular lens at the time of deriving a target value of an aberration of an intraocular lens from an aberration in cornea and anterior chamber portion and a set value of an aberration of the whole eyeball and determining a shape of the intraocular lens so that the aberration of the intraocular lens coincides with the target value.

That is, the present invention relates to an intraocular lens design method including deriving a target value of an aberration of an intraocular lens from an aberration of cornea and anterior chamber portion and a set value of an aberration of the whole eyeball and determining a shape of the intraocular lens so that at least the aberration of the intraocular lens coincides with the target value. Here, the aberration of the intraocular lens is an aberration of the intraocular lens in a case where predetermined convergent light enters the intraocular lens.

According to this method, since the shape of the intraocular lens may be determined based on a value of the aberration of the intraocular lens at the actual usage state, it is possible to coincide the aberration of the whole eyeball with the set value with high accuracy when the intraocular lens is actually inserted into the eyeball. As a result, it is possible to recover visual quality of a patient more reliably and as scheduled by an insertion surgery of the intraocular lens into the eyeball.

In the present invention, furthermore, the predetermined convergent light may be convergent light obtained by a convergence of parallel light through the cornea and the anterior chamber portion. According to this method, it is possible to determine the shape of the intraocular lens with higher accuracy on the basis of the value of the aberration at the actual usage state.

In the present invention, furthermore, the intraocular lens may form an intraocular lens group made up of a plurality of intraocular lenses having different powers and, with respect to each intraocular lens of the intraocular lens group, the shape of the each intraocular lens may be determined so that the aberration of the intraocular lens coincides with the target value.

Here, as described above, the intraocular lens may be required to be designed and manufactured as a lens group, in which a plurality of the intraocular lenses having different powers (focal point distance) between +30D and +6D are arranged, so as to select the power depending on a diopter scale of a patient. Therefore, according to the present invention, it is possible to insert the intraocular lens having a constant aberration even when the diopter scale of the patient has any value by determining the shape of the intraocular lens so that the aberration of the intraocular lens coincides with the target value with respect to each intraocular lens of the intraocular lens group. As a result, it is possible to reduce variation of visual quality of the patient after the surgery and to uniform surgery quality.

In the present invention, furthermore, the convergent light converged through the cornea and the anterior chamber portion may be focused on a point apart from a rear face of the cornea by 30.2 mm. Here, in a general ophthalmic inspection device, a diameter ($\phi$) of a light flux allowed to enter the cornea is 6 mm in general, the power of the cornea in an eye of an average human is 43D, and a spherical aberration of the cornea is about +0.28 μm. In this condition, it is understood that the convergent light converged through the cornea and the anterior chamber portion is focused on a point apart from a rear end of the cornea by 30.2 mm. Therefore, according to the present invention, it is possible to effectively design the intraocular lens adoptive to the eye of the average human.

In addition, the present invention may be an intraocular lens designed using the design method of the above-described intraocular lens. In addition, the present invention may be an intraocular lens group designed using the design method of the above-described intraocular lens.

Furthermore, the above-described solutions to the problems of the present invention can be used in combination with one another as much as possible.

Advantageous Effects of Invention

According to the present invention, a design work in a design of an intraocular lens can be simplified and the aberration in the whole eyeball can also be conformed to a target value with higher accuracy at the time of inserting the designed intraocular lens into an eyeball of a patient.

DESCRIPTION OF EMBODIMENTS

An embodiment of the present invention will be described below with reference to accompanying drawings.

First Embodiment

Figure 1:
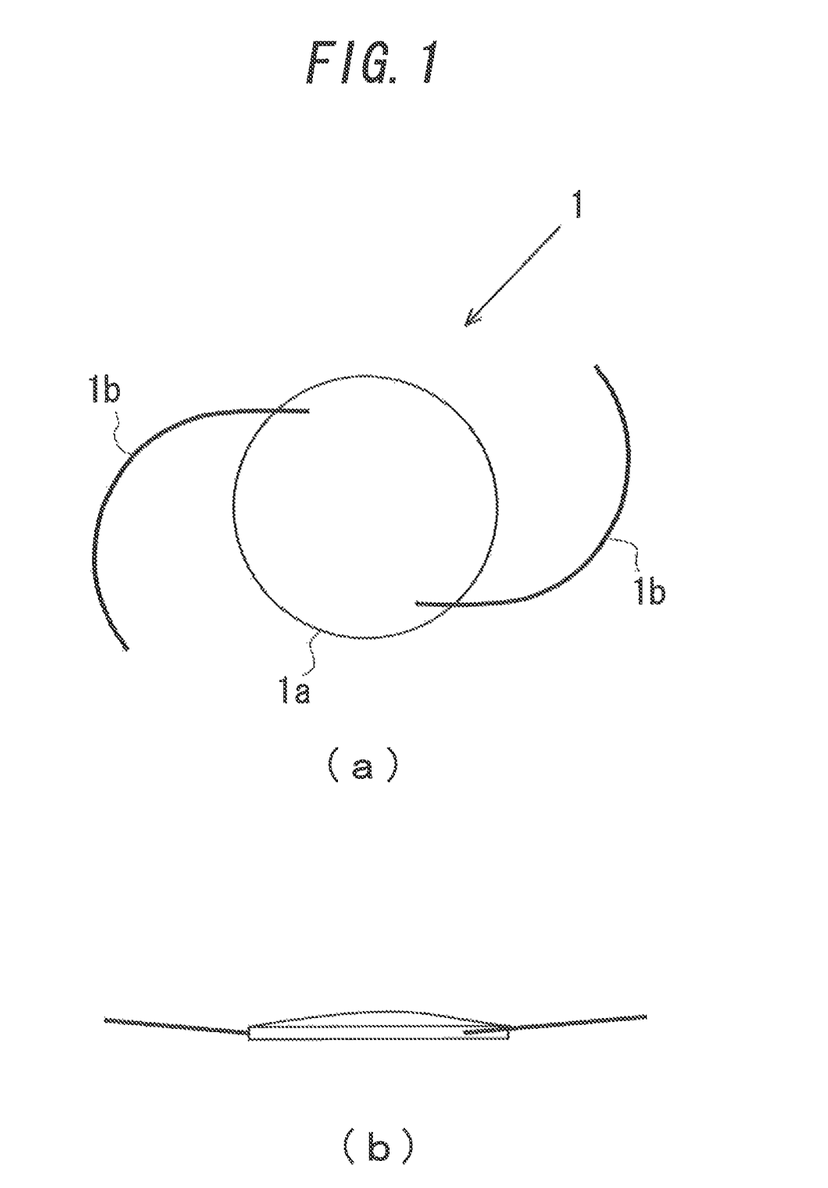
FIGS. 1a and 1b are diagrams illustrating a schematic configuration of an intraocular lens according to an embodiment of the present invention.

FIG. 1 is a diagram illustrating a schematic configuration of an intraocular lens 1 which is an intraocular lens of three-piece type, as an example to which the present invention is applied. FIG. 1(a) is a plan view and, more specifically, is a diagram viewed from a front side of an optical axis. FIG. 1(b) is a side view and, more specifically, a diagram viewed from a direction vertical to the optical axis. The intraocular lens 1 is formed of a lens body 1a having a predetermined refractive power and two beard-shaped supporting units 1b and 1b which are provided in the lens body 1a to hold the lens body 1a within the eyeball. The lens body 1a is formed of a flexible resin material. Furthermore, the lens body 1a in the present embodiment is an aspheric lens having an aspheric shape so as to keep aberration low with a single lens. Obviously, the present invention is applicable to various ophthalmic lenses including one-piece intraocular lens in which the supporting unit and a lens unit are integrally configured with the same material, regardless of spherical lens and aspheric lens.

In a case of performing a design of this intraocular lens 1, there is a method of performing an optical simulation by inputting all of optical parameters of an eyeball tissue including cornea, anterior chamber portion, and the intraocular lens 1, but recently, a method of effectively designing using values of power and aberration of the cornea and the anterior chamber portion and a target value of the aberration of the intraocular lens 1 is performed.

Figure 2:
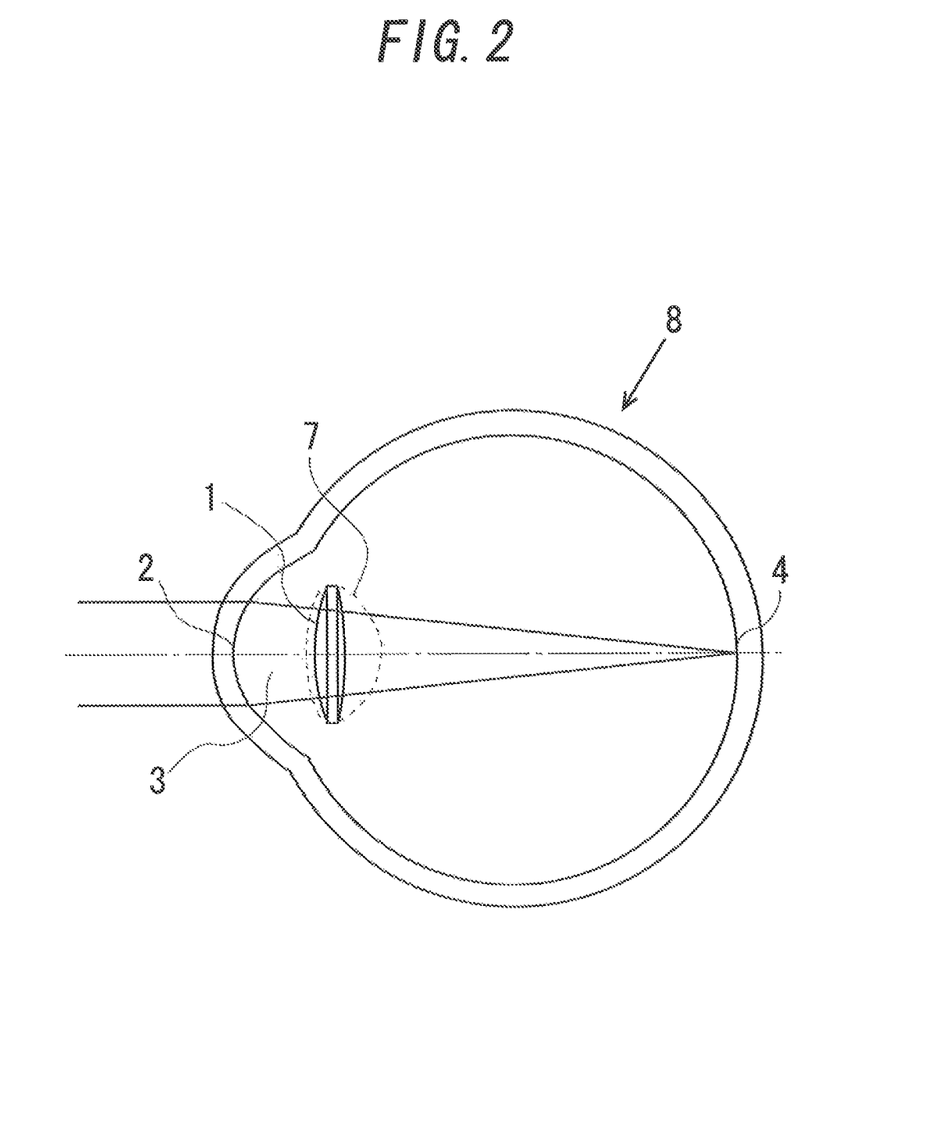
FIG. 2 is a diagram illustrating a schematic configuration within an eyeball of a human.

FIG. 2 illustrates a schematic diagram of a configuration of an eyeball 8 including the intraocular lens 1. In FIG. 2, the intraocular lens 1 is inserted into the eyeball 8 in place of an original crystalline lens 7. As a usage environment of the intraocular lens 1, it may be approximated as the lens is placed in the water. Then, light converged through a cornea 2, an anterior chamber portion 3, and the intraocular lens is converged on a retina 4. In addition, the aberration occurs when the light passes through each tissue of the eyeball 8, but between an aberration AbL of the intraocular lens 1 in water, an aberration AbE of the whole eyeball 8, and an aberration AbC of the cornea 2 and the anterior chamber portion 3, the following relation is satisfied.

$$AbL = AbE - AbC \quad (3)$$

Here, the AbE represents an aberration value of the whole eyeball 8 after an insertion of the intraocular lens 1. A designer of the intraocular lens 1 initially sets the aberration AbE of the whole eyeball 8 in conformity to a patient and determines the target value of the aberration of the intraocular lens 1 based on formula (3).

For example, when intending to cancel the aberration of other parts by inserting the intraocular lens 1 into the eyeball 8 of the patient, the designer sets the target value of the aberration of the intraocular lens 1 so that the aberration AbE of the whole eyeball 8 becomes zero. Furthermore, aberration AbC of the cornea is an aberration which is generated by a lens effect due to the cornea 2 and the anterior chamber portion 3. The AbC value can be obtained by actually measuring the shape of the cornea 2. For example, a representative value of the aberration AbC of the cornea 2 and the anterior chamber portion 3 is +0.28 μm. In this case, for example, the target value of the aberration AbL of the intraocular lens 1 comes to −0.28 μm so that the aberration AbE of the whole eyeball 8 becomes 0 μm. In addition, for example, the target value of the aberration AbL of the intraocular lens 1 comes to −0.04 μm so that the aberration AbE of the whole eyeball 8 is consciously left to become +0.24 μm.

In a design work of the actual intraocular lens 1, the shape of the intraocular lens 1 is determined with a correction of a virtual shape of the intraocular lens 1 by trial and error until the above-determined aberration AbL of the intraocular lens 1 is obtained. Then, when inspecting the aberration of the intraocular lens 1 after the manufacture, the designer fixes the intraocular lens 1 having the shape determined by the above-described method in the water and places an optical system corresponding to the cornea 2 and the anterior chamber portion 3 in front of the intraocular lens 1 to measure the aberration at a convergence point by allowing parallel light coming from infinity to enter the optical system corresponding to the cornea 2 and the anterior chamber portion 3. Then, the designer inspects whether the difference between the measured aberration and the target value of the AbL is within a reference value.

In the related art, however, when the shape of the intraocular lens 1 is determined by the trial and error, the simulation is performed in such a manner that the aberration is calculated on the assumption that the parallel light enters the intraocular lens 1 and make the calculated aberration coincide with the target value of the AbL. In contrast to this, in the tissue within the actual eyeball 8, the light entering the intraocular lens 1 is not the parallel light but convergent light refracted by the cornea 2 and the anterior chamber portion 3. In the method of the related art, therefore, when the designed intraocular lens 1 is inserted into the eyeball 8 of the patient, there was a disadvantageous case in which the aberration AbE of the whole eyeball 8 did not reach a set value.

In the present embodiment, on the other hand, a process of determining the shape of the intraocular lens 1 by the trial and error is to simulate on the assumption that the convergent light refracted by the cornea 2 and the anterior chamber portion 3 enters the intraocular lens 1. Thus, it is possible to simulate under the condition closer to the inside of the actual eyeball 8 and to determine the shape of the intraocular lens 1 so that the aberration AbE of the whole eyeball 8 coincides with the set value with higher accuracy.

Figure 3:
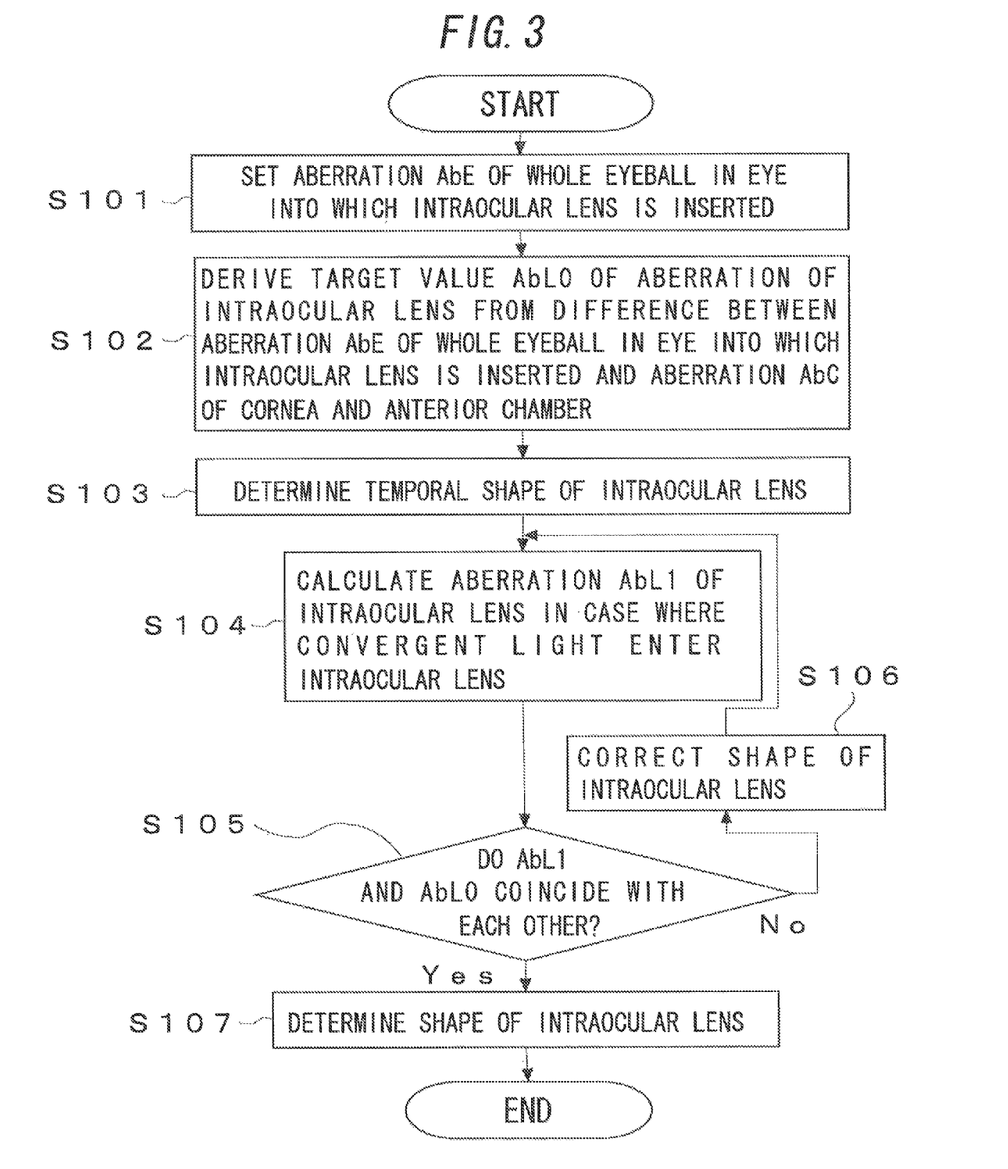
FIG. 3 is a flowchart illustrating a design routine of the intraocular lens according to the embodiment of the present invention.

FIG. 3 illustrates a flowchart of a design routine of intraocular lens according to the present embodiment. When the present routine is executed, first, in S101, an aberration of an ocular fundus (aberration AbE of the whole eyeball 8) in the eye into which the intraocular lens 1 is inserted is set in conformity to the patient. Specifically, the value of AbE differs depending on the eye situation of the patient, but may be set to 0 μm so that the aberration is completely canceled, for example, and there are instances where the aberration is consciously left. When the aberration AbE of the whole eyeball 8 is set to 0 μm, there are disadvantages that a focus depth is shallow, a focus is easily deviated, and an impact of the eccentricity of the intraocular lens 1 in an insertion surgery tends to be large. Accordingly, it may be preferable to leave the aberration to some extent, for example, about 0.1 to 0.3 μm so as to deepen the focus depth and strengthen to the eccentricity. When the process of S101 is completed, the process proceeds to S102.

In S102, a target value AbL0 of the aberration of the intraocular lens 1 is derived from the difference between the set value AbE of the aberration of the whole eyeball 8 and the aberration AbC of the cornea 2 and the anterior chamber portion 3 based on formula (3). Here, the aberration AbC of the cornea 2 and the anterior chamber portion 3 is derived by actually measuring the shape of the cornea 2. When the process of S102 is completed, the process proceeds to the simulation of S103 and the subsequent steps.

In S103, a temporary shape of the intraocular lens 1 is determined. That is, a first shape is determined so as to determine the shape of the intraocular lens 1 by the trial and error. When the process of S103 is completed, the process proceeds to S104.

In S104, an aberration AbL1 of the intraocular lens 1, in case where the convergent light obtained by refraction of the parallel light through the cornea and the anterior chamber portion 3 enters the intraocular lens 1 based on the shape at the present moment, is calculated. This calculation is performed based on a power of the cornea 2 and the anterior chamber portion 3 and the shape of the intraocular lens 1. Furthermore, the power of the cornea 2 and the anterior chamber portion 3 can be derived by actually measuring the shape of the cornea 2. More specifically, the convergent light obtained by refraction of the parallel light through the cornea 2 and the anterior chamber portion 3 may be defined as convergent light where light is focused on a point apart from a rear end of the cornea 2 by, for example, 30.2 mm. This is a value based on the distance up to a focal point of the convergent light which passes through the average cornea 2 and anterior chamber portion 3. When the process of S104 is completed, the process proceeds to S105.

In S105, it is determined whether or not the aberration AbL1 of the intraocular lens 1 calculated in S104 coincides with the target value AbL0 of the aberration of the intraocular lens 1 which is set in S101. More specifically, for example, when the AbL1 is within a range of AbL0±0.02 μm, it may be determined that the AbL1 and the AbL0 coincide with each other. Naturally, a threshold value of whether or not the AbL1 and the AbL0 coincide with each other is not limited to ±0.02 μm. Here, when it is determined that the AbL1 and the AbL0 do not coincide with each other, the process proceeds to S106. On the other hand, when it is determined in S105 that the AbL1 and the AbL0 coincide with each other, the process proceeds to S107.

In S106, the shape of the intraocular lens 1 is determined once again so as to correct in a direction which brings the AbL1 close to AbL0 on the basis of a comparison result between the aberration AbL1 of the intraocular lens 1 and the target value AbL0 of the aberration of the intraocular lens 1 in S105. Then, the process returns to the front of S104. As a result, the process of S104 to S106 is repeatedly performed until it is determined in S105 that the AbL1 and the AbL0 coincide with each other.

In S107, the shape of the intraocular lens 1 at the present moment is determined as a final value. When the process of S107 is completed, the present routine is ended once.

According to the above-described design routine of intraocular lens, the shape of the intraocular lens 1 can more easily be determined on the basis of the power and the aberration of the cornea 2 and the anterior chamber portion 3 and the set value of the aberration of the whole eyeball 8. Further, since the aberration of the intraocular lens 1 is calculated on the assumption that the convergent light refracted through the cornea 2 and the anterior chamber portion 3 enters instead of the parallel light as used in the related art, the intraocular lens 1 can be designed in conformity with reality.

In addition, when designing and manufacturing the intraocular lens 1 in practice, it is necessary to design and manufacture as a lens group, in which a plurality of intraocular lenses 1 having different powers (focal point distance) between +30D and +6D are arranged, so as to select the power depending on a diopter scale of the patient. With respect to each intraocular lens 1 of the intraocular lens group, accordingly, it is possible to provide the intraocular lens 1 having a constant aberration even when the diopter scale of the patient has any value by determining the shape of the intraocular lens 1 with the design routine of intraocular lens so that the aberration coincides with the target value.

Figure 4:
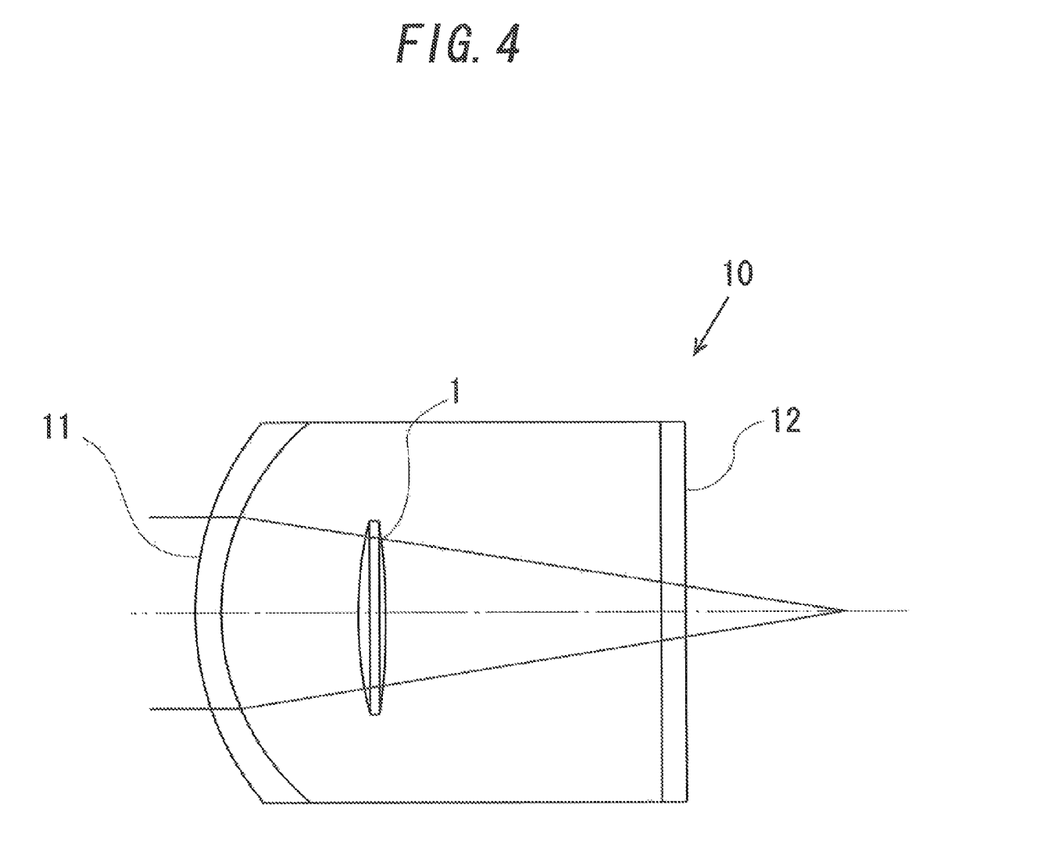
FIG. 4 is a diagram explaining an inspection method of the intraocular lens according to the embodiment of the present invention.

Next, an inspection method of the aberration of the intraocular lens 1 designed using the design routine of intraocular lens described above will be described. As illustrated in FIG. 4, a pseudo eyeball 10 is configured in such a manner that the water is filled in a space sandwiched between a cornea lens 11 designed in conformity to the characteristics of the cornea and the anterior chamber portion and a flat glass 12 and then the intraocular lens 1 designed by the method described above is fixed in the water, and thus the aberration of the intraocular lens 1 is measured using a wavefront aberration measurement device which is not illustrated in the drawings. In FIG. 4, the cornea lens 11 is a meniscus aspheric lens which generates the convergent light similar to the convergent light due to the average cornea and anterior chamber portion.

Here, at the state with the exception of the intraocular lens 1 from the pseudo eyeball 10, the aberration of the cornea lens 11 has 1/20 or less with respect to the target value of the aberration of the intraocular lens 1 to be inspected, when the parallel light having a diameter ($\phi$) of 6 mm with a wavelength ($\lambda$) of 546 nm enters. By measuring the aberration at a state in combination of the cornea lens 11 due to the meniscus aspheric lens and the intraocular lens 1, it is possible to measure the aberration of the intraocular lens 1 when the convergent light enters. Furthermore, the aberration of the cornea lens 11 may not necessarily be required to have 1/20 or less of the target value of the aberration in the intraocular lens 1. However, when the aberration of the cornea lens 11 has a value larger than 1/20 of the target value of the aberration in the intraocular lens 1, after separately measuring the aberration of the single cornea lens 11, it is necessary to subtract the aberration of the single cornea lens 11 from the measurement result obtained using the pseudo eyeball 10.

Figure 5:
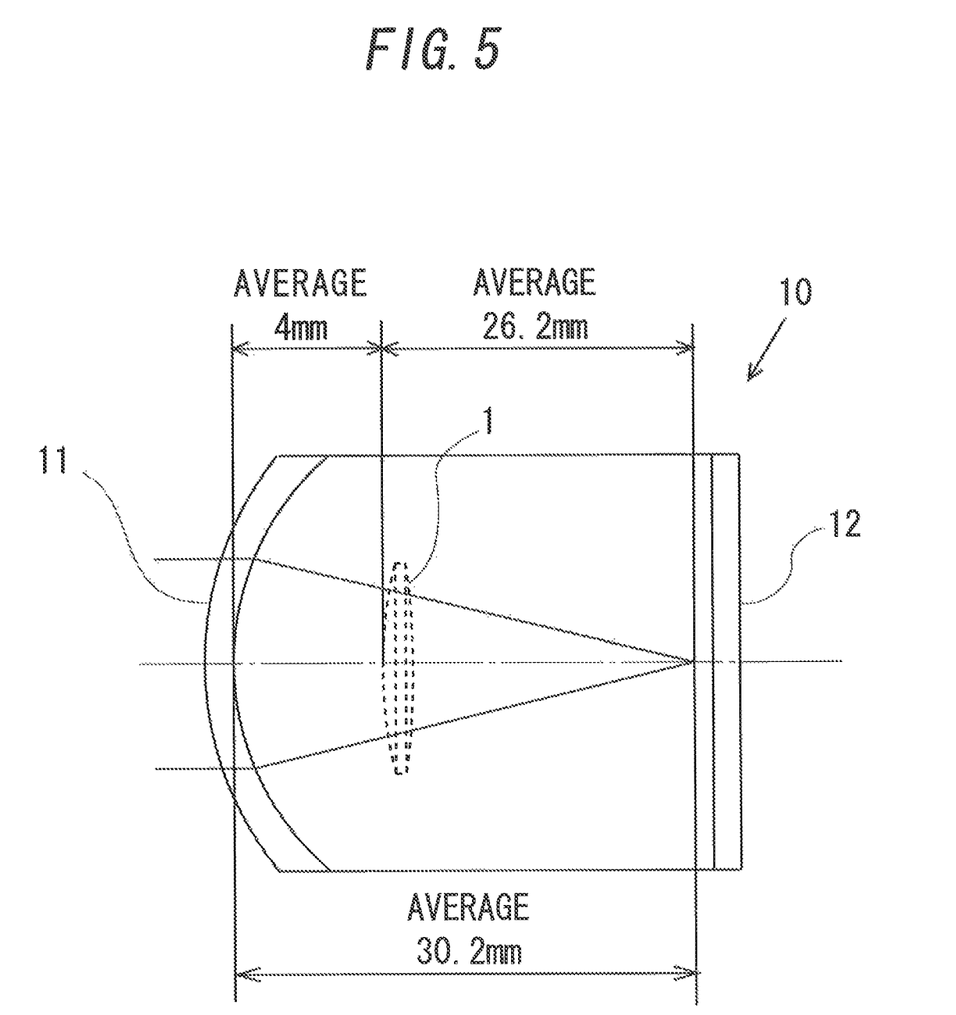
FIG. 5 is a diagram explaining a detailed dimension relation of a pseudo-eyeball according to the embodiment of the present invention.

In FIG. 5, a dimensional relation of the pseudo eyeball 10 will be described in detail. The pseudo eyeball 10 is obtained by reproducing an optical system inside the average eyeball 8. The power of the cornea lens 11 due to the meniscus aspheric lens is 43D, and a spherical aberration is +0.28 µm. In addition, a diameter ($\phi$) of light flux used for the inspection is 6 mm. Further, when the intraocular lens 1 is not attached, a focal position of the cornea lens 11 is located at a position apart from the rear end face of the meniscus aspheric lens by 30.2 mm. This is a value determined based on the distance from the rear end face of the average cornea 2 to the retina 4 in the actual eyeball 8. In addition, since the present embodiment is premised that the convergent light assumed in S104 of the design routine of intraocular lens is focused on the point apart from the rear end of the cornea 2 by 30.2 mm, it is possible to inspect the aberration of the intraocular lens 1 designed based on the convergent light due to the average cornea 2 and anterior chamber portion 3 under the same conditions. As a result, it is possible to inspect with higher accuracy and to feed back securely the inspection result to the design according to the design routine of intraocular lens.

In the actual eyeball 8 of the human, furthermore, the power and the spherical aberration in the cornea 2 and the anterior chamber portion 3 can take various values. For example, when the power in the cornea 2 and the anterior chamber portion 3 is distributed from 30D to 60D and the spherical aberration is distributed from +0.1 to +0.5 µm, the distance between the rear end face of the cornea 2 and the focal point is varied between 17 mm and 45 mm. Therefore, the focal position of the cornea lens 11 may be appropriately determined within this range.

Figure 6:
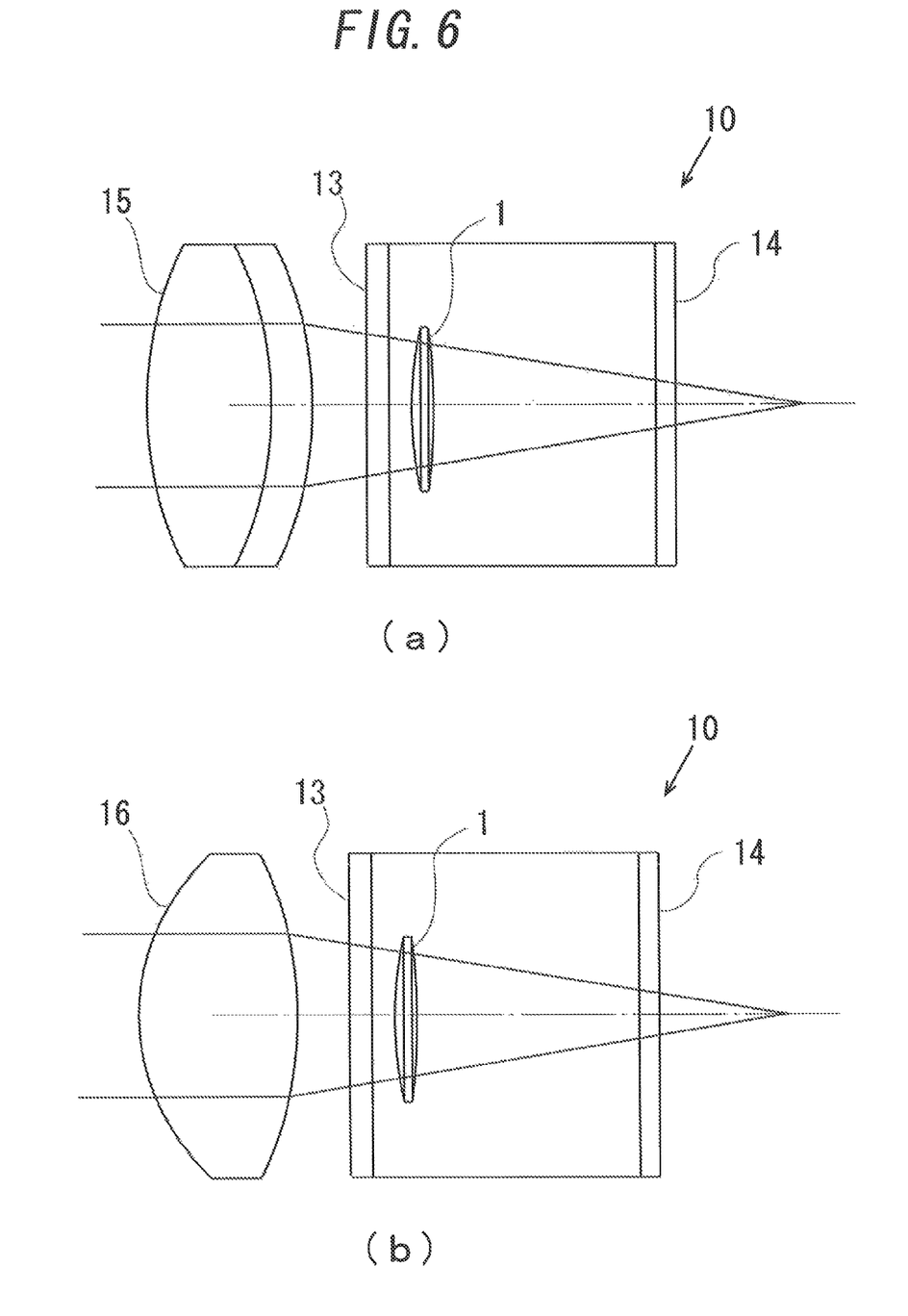
FIGS. 6a and 6b are diagrams illustrating another example of a pseudo-eyeball according to the embodiment of the present invention.

In addition, an example using the meniscus aspheric lens as the cornea lens 11 is described above, but the configuration of the pseudo eyeball 11 is not limited thereto. For example, as illustrated in FIG. 6 (a), the intraocular lens 1 may be fixed in the water which is filled in the space sandwiched between two flat glasses 13 and 14, and a cornea lens 15 may be configured in the air by a doublet spherical lens. In addition, as illustrated in FIG. 6 (b), the intraocular lens 1 may be fixed in the water which is filled in the space sandwiched between two flat glasses 13 and 14, and a cornea lens 16 may be configured in the air by a singlet aspheric lens. Furthermore, in this case, the cornea lenses 15 and 16 are required to be designed in consideration of the refraction due to the flat glass 13.

Furthermore, when the aberration of each intraocular lens 1 of the lens group in which each intraocular lens 1 is designed by the design routine of intraocular lens is inspected using the inspection method of the present embodiment, the aberration of each intraocular lens 1 must be aligned with the AbL0 derived in S102 with good accuracy. On the other hand, with respect to each intraocular lens of the intraocular lens group designed using the aberration value of the intraocular lens 1 in a case where the parallel light enters as in the related art, when tested by the above-described method, the inspection result must be out of the AbL0 derived in S102 or deviation must be increased largely.

Alternatively, when the aberration of each intraocular lens 1 of the lens group in which each intraocular lens 1 is designed by the above-described design routine of intraocular lens is inspected in such a manner that the parallel light enters the intraocular lens 1, the aberration of each intraocular lens 1 must be out of the AbL0 derived in S102 or the deviation must be increased largely. On the other hand, with respect to each intraocular lens of the intraocular lens group designed using the aberration value of the intraocular lens 1 in a case where the parallel light enters as in the related art, when the aberration of each intraocular lens is inspected in such a manner that the parallel light enters, the deviation of the inspection result is likely to become lower compared with the case of designing each intraocular lens 1 by the above-described design routine of intraocular lens.

REFERENCE SIGNS LIST

1 Intraocular Lens
1a Lens Body
1b Supporting Unit
2 Cornea
3 Anterior Chamber Portion
4 Retina
8 Whole Eyeball
10 Pseudo Eyeball 11 Cornea Lens
12, 13, 14 Flat glass

What is claimed is:

1. An intraocular lens design method, comprising:
deriving a target value AbL of an aberration of an intraocular lens from an aberration AbC of a cornea and an anterior chamber portion and a set value of an aberration AbE of the whole eyeball into which the intraocular lens is inserted;
determining an initial shape of the intraocular lens;
determining an aberration value for the intraocular lens having the initial shape;
iteratively adjusting the initial shape of the intraocular lens so that at least the aberration of the intraocular lens coincides with the target value; and
obtaining parameters associated with a target shape of the intraocular lens,
wherein the target value AbL is derived from the difference between the set value of the aberration AbE of the whole eyeball and the aberration AbC of the cornea and the anterior chamber portion, based on formula AbL=AbE−AbC,
wherein the aberration AbC of the cornea and the anterior chamber portion is derived by measuring the shape of the cornea,
wherein the aberration of the intraocular lens is determined by allowing a predetermined converging beam of light to enter the intraocular lens, the predetermined converging beam of light obtained by focusing a parallel beam of light that is incident on a front surface of the cornea to a focal point at a distance of 17 mm-45 mm from a rear surface of the cornea,
wherein the obtained parameters are used by a lens manufacturer to manufacture an intraocular lens having the target shape.

2. The intraocular lens design method according to claim 1, wherein the intraocular lens forms an intraocular lens group made up of a plurality of intraocular lenses having different powers and, with respect to each of the intraocular lenses of the intraocular lens group, the shape of each of the intraocular lenses is determined so that the aberration of the intraocular lens coincides with the target value.

3. An intraocular lens group in which each intraocular lens is designed by the intraocular lens design method according to claim 2.

4. The intraocular lens design method according to claim 2, wherein the converging beam of light is focused at a focal point at a distance of approximately 30 mm from the rear surface of the cornea.

5. An intraocular lens that is designed by the intraocular lens design method according to claim 4.

6. The intraocular lens design method according to claim 1, wherein the converging beam of is focused at a focal point at a distance of approximately 30 mm from the rear surface of the cornea.

7. An intraocular lens that is designed by the intraocular lens design method according to claim 6.

8. An intraocular lens that is designed by the intraocular lens design method according to claim 1.

* * * * *